United States Patent [19]

Herscovici et al.

[11] Patent Number: 4,462,407
[45] Date of Patent: Jul. 31, 1984

[54] DUAL CHANNEL CARDIAC PACER ISOLATION CIRCUIT

[75] Inventors: Hari Herscovici, Miami Beach; Peter P. Tarjan, Miami, both of Fla.

[73] Assignee: Cordis Corporation, Miami, Fla.

[21] Appl. No.: 375,040

[22] Filed: May 5, 1982

[51] Int. Cl.³ .............................................. A61N 1/36
[52] U.S. Cl. ...................... 128/419 PG; 128/419 PS
[58] Field of Search .................. 128/419 PG, 419 PS, 128/419 P

[56] References Cited

U.S. PATENT DOCUMENTS

| | | | |
|---|---|---|---|
| 3,135,264 | 6/1964 | Tischler et al. | 128/423 |
| 3,209,081 | 9/1965 | Ducote et al. | 128/419 PS |
| 3,669,120 | 6/1972 | Nielsen | 28/419 PG |
| 3,698,398 | 10/1972 | Berkovits | 128/419 PG |
| 3,903,897 | 9/1975 | Woollons et al. | 128/419 PG |
| 4,114,627 | 9/1978 | Lewyn et al. | 128/419 PT |
| 4,289,134 | 9/1981 | Bernstein | 128/419 PG |
| 4,300,566 | 11/1981 | Stindt et al. | 128/419 PG |
| 4,328,807 | 5/1982 | Jirak et al. | 128/419 PG |

Primary Examiner—William E. Kamm
Assistant Examiner—Mitchell J. Shein
Attorney, Agent, or Firm—Kenway & Jenney

[57] ABSTRACT

To prevent crosstalk between atrial and ventricular bipolar cardiac pacer leads, separate input/output circuits for the two channels are powered by respective isolated capacitors. In one embodiment, the capacitors are resistively coupled to the pacer battery for continuous charging. In another embodiment, one side of each capacitor is normally disconnected from the pacer battery. Charging switches momentarily connect one or the other capacitor directly to the battery in response to the output of the corresponding sense amplifier.

21 Claims, 6 Drawing Figures

DUAL CHANNEL CARDIAC PACER ISOLATION CIRCUIT

CROSS-REFERENCE TO RELATED APPLICATION

The subject matter of this application is related to that of U.S. patent application Ser. No. 375,039 entitled "Dual Channel Cardiac Pacer Isolation Circuit", filed simultaneously herewith, by the same inventors, assigned to the assignee of the present application and incorporated by reference herein.

BACKGROUND OF THE INVENTION

The invention relates generally to cardiac pacers, and more particularly to means for preventing crosstalk between bipolar pacer leads.

There are two major pumping chambers in the heart, the left and right ventricles. Simultaneously contracting, these chambers expel blood into the aorta and the pulmonary artery. Blood enters the ventricles from the left and right atria, respectively. The contractions arise from a wave of electrical excitation which begins in the right atrium and spreads to the left atrium. The excitation enters the atrio-ventricular (AV) node which delays its passage via the bundle of His into the ventricles. The atria contract in a separate action which precedes the major ventricular contraction by an interval of about 100 milliseconds (ms), known as the AV delay. In the healthy heart, atrial contractions begin every 400–1,000 ms at a steady metabolically determined frequency known as the "sinus" rate, which increases automatically with exercise, the AV delay being foreshortened at higher rates.

Electrical signals corresponding to the contractions appear in the electrocardiagram. A signal known as the P-wave accompanies the atrial contraction while a signal known as the QRS complex, with a predominant R-wave, accompanies the ventricular contraction. The P and R-waves can be reliably detected as timing signals by electrical leads in contact with the respective heart chambers.

The typical implanted cardiac pacer operates by producing electrical stimulation pulses to supply missing excitation via an insulated wire (or "pacing lead") terminating in an electrode attached to the right ventricle. The R-wave can be sensed by the same lead to inhibit or trigger stimulation or to restart a timing interval as in "demand" pacing. An additional lead contacts the atrium to sense P-waves, if desired. Pacers whose ventricular stimulation is timed from the sensing of a P-wave are referred to as AV synchronous or "physiological" pacers since they preserve the natural sinus rate as well as the normal sequence of contractions. In AV sequential pacers, sometimes the atrial lead is also used for atrial stimulation. Examples of physiological AV sequential pacers or "double demand" pacers in which the atrial and ventricular leads can both stimulate and sense are shown in pending U.S. patent application Ser. No. 153,422 entitled "Ventricular Inhibited Cardiac Pacer" filed May 27, 1980 and U.S. patent application Ser. No. 207,003 entitled "Multi-Mode Microprocessor Based Programmable Cardiac Pacer" filed Nov. 14, 1980, both assigned to the assignee of the present application, and incorporated herein by reference in their entirety.

There are two basic types of electrode systems used in pacing leads. Unipolar leads terminate distally in a single electrode (cathode) and employ the case of the pulse generator itself, or a conductive plate on the case, as the return electrode or ground (anode). Bipolar pacing leads, on the other hand, terminate distally in two spaced insulated electrodes connected to the pulse generator through respective wires in the pacing lead. Thus, each bipolar lead carries a positive and negative electrode for the respective chamber, and the case is not designed to form a part of the electrical circuit in this configuration.

In an AV sequential bipolar lead pacing system, bipolar pacing leads extend into the right atrium and right ventricle. In a pacer having a common ground connection, the two positive electrodes on the respective bipolar leads are tied together electrically. This shared ground connection can present crosstalk problems in both sensing and stimulation when each bipolar lead is in a different heart chamber. This is an extremely important problem to solve for physiological pacers which provide bipolar stimulation and sensing for both heart chambers with the same implanted pacer powered by a single battery.

One of the ways previously used to accomplish some measure of isolation between bipolar leads is to employ a transformer in the output stage of the pacing circuit to isolate the lead electrodes. This approach, however, has only been practical when sensing is done only on one channel. In addition, it has the serious drawback of adding a relatively bulky inefficient component to the otherwise miniaturized pacer electronics.

SUMMARY OF THE INVENTION

The general objective of the invention is to alleviate crosstalk between bipolar pacing leads in different heart chambers reliably and with minimum additional circuitry. This objective is accomplished by supplying power to atrial and ventricular input/output circuits from respective capacitors which are electrically isolated from the main pacer power supply, as well as from each other. In one embodiment, the capacitors are resistively coupled to the pacer battery for continuous charging. In another embodiment, one side of each capacitor is normally disconnected from the pacer battery. Respective pairs of charging switches connect one or the other capacitor directly to the battery momentarily in response to the output of the corresponding sense amplifier during the pacing cycle. Each capacitor is connected to reference potential to maintain logic levels at all times except whenever the other capacitor is charging. In the preferred embodiments the pacing logic input from the atrial sense amplifier is blocked in the presence of an output from the ventricular sense amplifier to avoid the naturally cross-coupled R-wave.

DESCRIPTION OF THE PREFERRED EMBODIMENT

Figure 1:
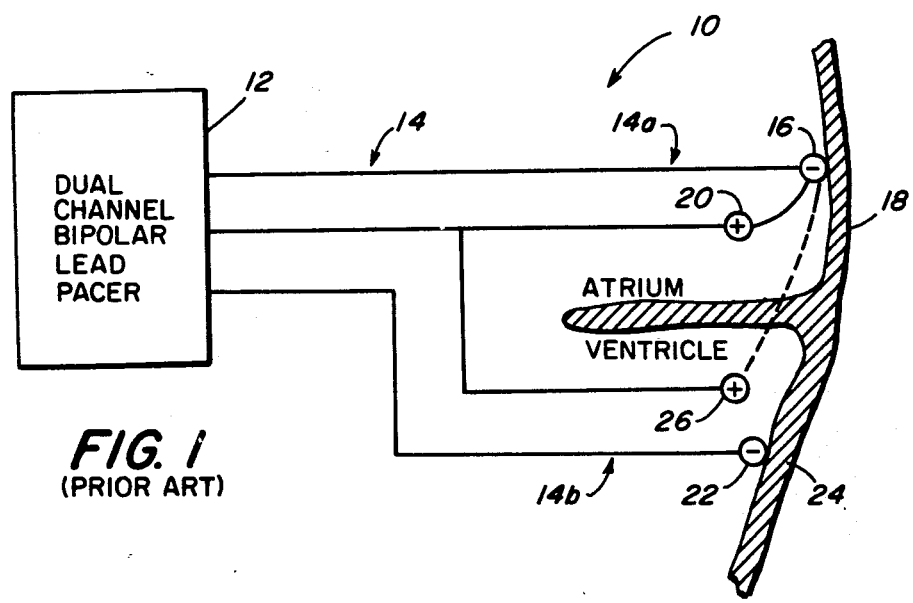
FIG. 1 is a schematic representation of a prior art AV sequential bipolar pacing system.

FIG. 1 shows an AV sequential bipolar lead pacing system 10 including a double demand cardiac pacer pulse generator 12 containing the pacing logic circuitry sealed together with the battery cells in the customary biologically compatible hermetic enclosure. The pacer pulse generator 12 itself is implanted at a suitable location in the body, such the axillary region, and is electrically interconnected with a three conductor pervenous pacer lead 14 which terminates distally in an atrial lead 14a having a negative electrode 16 in contact with the inside of the right atrium 18 and a positive electrode or anode 20 spaced from the cathode. The ventricular portion 14b of the pacer lead terminates in a negative electrode 22 in contact with the ventricular wall 24 and a spaced anode 26. The anodes 20 and 26 share a common electrical connection and are thus at the same reference potential. In sensing, a "spurious" electrical potential can be established by the heart itself between the ventricular anode 26 and the atrial cathode 16 resulting in a signal to the pacer which appears to have originated in the atrium alone. The electrical path (upper dashed arrow in FIG. 1) between atrial electrodes 16 and 20 offers less resistance, of course, and is therefore the expected site of stimulation when the pacer pulse generator 12 applies an electrical potential between these electrodes. However, the ventricular anode 26 may inadvertently become part of the electrical circuit and cause undesirable cross stimulation. The same type of crosstalk on sensing or stimulation can occur on the ventricular channel through cathode 22 in relation to anodes 20 and 26.

Figure 2:
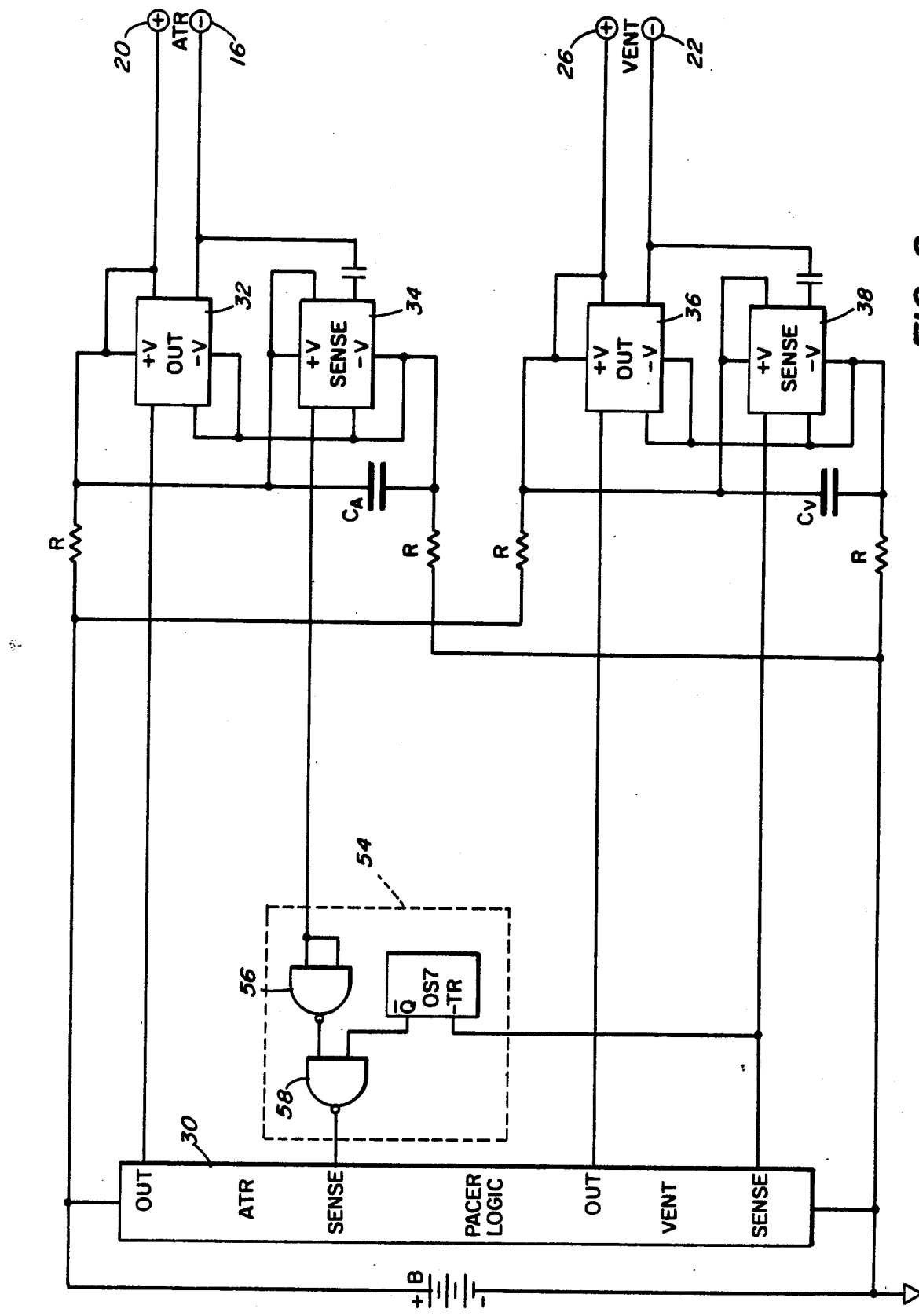
FIG. 2 is a block and electrical schematic diagram of a resistively coupled capacitor isolation circuit for a dual channel bipolar cardiac pacer according to the invention.

A solution to this problem is shown by the circuit of FIG. 2 which creates two separate "energy reservoirs" supplied with the necessary energy adjustments from the pacer's battery B through resistors R. In this embodiment, the pacing lead has four conductors (one for each electrode) and the remaining circuitry is sealed within the pulse generator enclosure along with the battery. Atrial and ventricular pacing logic 30 is separated from the input/output circuitry comprising atrial output and sense amplifiers 32 and 34 and ventricular output and sense amplifiers 36 and 38. The CMOS pacing logic 30 is powered directly by battery B. The input/output circuitry is powered by atrial and ventricular capacitors $C_A$ and $C_V$ which in turn are charged by the battery B. As shown in FIG. 2, opposite sides of each capacitor are connected to the battery by respective isolation resistors R, which may be of substantially identical resistance, for example, 15 kilohms. The resistors connecting each capacitive "reservoir" to the power supply should be large enough to isolate the corresponding channel from the other channel. The sense amplifier circuits 34 and 34 include the usual comparators (not shown) which threshold detect the magnitude of the amplifier outputs to produce a digital signal indicative of atrial or ventricular electrical activity.

The value of the capacitor ($C_A$ or $C_V$) which determines the time constant of the charging circuit, should be chosen so that the energy delivered during an output pulse of the maximum current amplitude is completely recovered in the charge obtained between output pulses at the maximum rate. If R is 15 kilohms, for example, the isolation between the two positive electrodes 20 and 26 is a total of 30 kilohms. This resistance is large enough to avoid any cross stimulation since the equivalent resistance of the heart is only on the order of 600 ohms. For sensing, the 30 kilohms resistance with the heart equivalent circuits will not change the heart charge distribution significantly. Thus, this circuit avoids cross sensing problems as well. The interface between the input/output circuitry and the pacing logic 30 does have 15 kilohms in series. However, since the pacing logic 30 is CMOS circuitry, logic signal levels are adequately maintained.

Figure 3:
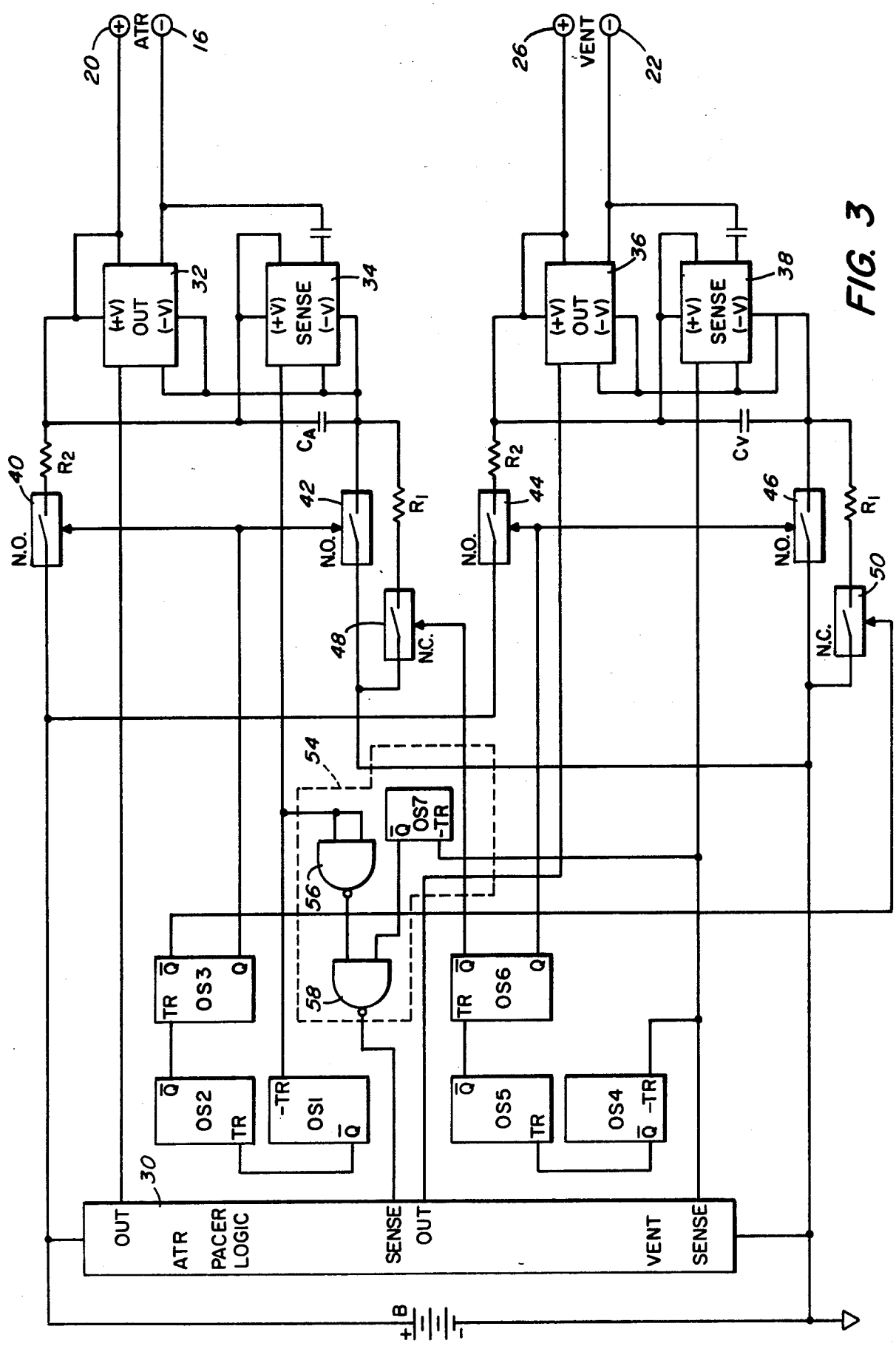
FIG. 3 is a block and electrical schematic diagram of a switch coupled capacitor isolation circuit for a dual channel bipolar cardiac pacer according to the invention.

In the alternative embodiment of FIG. 3, the separation between the pacing logic 30 and input/output circuitry 32, 34, 36 and 38 is accomplished by means of four analogic switches which can be MOSFET transistors as well as complementary metal oxide semiconductor (CMOS) analog switches 40, 42, 44 and 46, which are actuated by logic circuitry triggered by the output of either sense amplifier 34 or 38. Atrial capacitor $C_A$ is connected to the positive side of battery B through switch 40 and series resistor $R_2$. The other side of this capacitor is connected to negative battery potential ("ground") through two paths, (1) normally open switch 42 and (2) resistor $R_1$ in series with normally closed switch 48. Because switch 40 is normally open, the power capacitor $C_A$ is normally completely disconnected from the positive side of the battery. The ventricular power capacitor $C_V$ is connected in a similar manner. Typical values of resistance and capacitance for the foregoing components of FIG. 3 are: $R_1$, 10 kilohms; $R_2$, 3 kilohms; and $C_A$ and $C_V$, 100 microfarads.

Separate charging logic for each channel in the circuit of FIG. 3 is triggered by the output of the corresponding sense amplifier. For example, an output from atrial sense amplifier 34 triggers monostable multivibrator ("one-shot") OS1 which has an astable refractory period of 160 ms. The output of OS1 immediately triggers a one-shot OS2 which has a 5 ms period. The trailing edge of the complementary output of one-shot OS2 triggers a third one-shot OS3 which has a 30 ms period. The complementary outputs of one-shot OS3 simultaneously close analog switches 40 and 42 and open switch 50 for a 30 ms period to enable the atrial capacitor $C_A$ to recharge. The charging time constant is fast because of the presence only of the smaller resistor $R_2$. Opening switch 50 in the ventricular channel disconnects capacitor $C_V$ from ground thus providing for isolation between the power capacitors during the brief recharging period. The ventricular charging logic (OS4, OS5 and OS6) operates in exactly the same manner as the atrial charging logic so that analog switches 44 and 46 close briefly following a ventricular sense amplifier output while the normally closed atrial channel switch 48 is interrupted.

The one-shot circuits and analog switches are supplied with voltage from the battery B. The outputs of the sense amplifiers 34 and 38 as well as the inputs to the output stages 32 and 36 are connected to the pacer's logic circuit 30 as in the circuit of FIG. 2.

Figure 4:
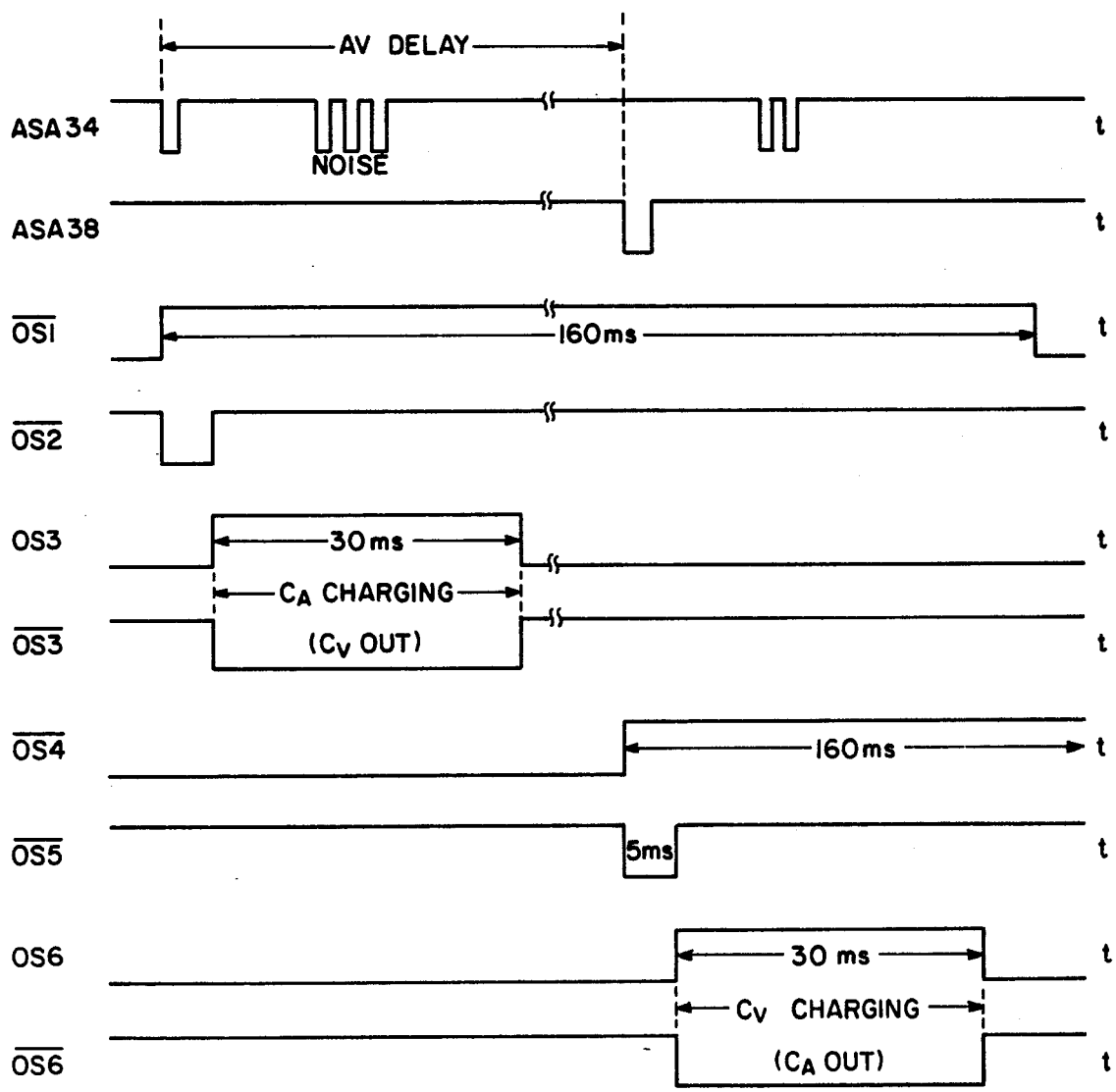
FIG. 4 is a timing diagram illustrating various signals in the circuitry of FIG. 3.

With reference to the timing diagram of FIG. 4, when the atrial sense amplifier 34 senses a heart pulse or is saturated by an output pulse from the pacer, the sense amplifier output goes low and triggers the first monostable OS1 (or OS4). The 160 ms refractory period avoids retriggering by a multipulse output of the sense amplifiers as shown, for example, for the atrial sense amplifier in the first line from the top in FIG. 4. In addition, the 160 ms period covers the normal AV delay so that at the time the ventricular contraction would normally occur, the charging logic is refractory. Spurious sense amplifier outputs can occur when a signal larger than 1 millivolt is sensed or when the amplifier's output saturates after a stimulation pulse is issued through the output stage. The 5 ms period of OS2 (or OS5) provides enough time for the sensed event to terminate following which the output of OS3 (or OS6) turns on the corresponding analog switches to charge capacitor $C_A$ (or $C_V$).

As in the circuit of FIG. 2, the capacitors $C_A$ and $C_V$ in the circuit of FIG. 3 represent substitution power supplies which provide energy for the input/output circuitry during heart or pacer events. After each capacitor is charged, the connection to positive battery voltage is interrupted by the corresponding open switch 40 or 44, or at least isolated by tens of megohms, the off resistance of a CMOS analog switch. The connection to ground (negative battery reference) is through a large resistance R1, for example, 10 kilohms. This resistance is large enough to limit the current through the circuit which includes heart tissue, to levels considerably lower than stimulation threshold to avoid cross stimulation. At the same time, however, the value of this resistor R1 is still suitable for the transfer of information between CMOS circuits. Thus binary signals are maintained at sufficient logic levels. For example, the output from the atrial side of the pacing logic 30 is a binary signal which commands the output stage 32 to issue a stimulation pulse. The output of the sense amplifier 34, on the other hand, is a binary signal from a comparator. Resistor R1 maintains the binary signal level at the sense input of the pacing logic 30.

The circuits of FIGS. 2 and 3 provide the necessary isolation so that the signals issued by the heart itself will be processed, as they are, without distortion. However, in many cases it happens that the R-wave developed in the ventricle actually produces a signal in the atrium too. This signal follows the P-wave signal originating in the atrium after the corresponding AV delay and has an amplitude generally lower than the P-wave. Yet, there are cases in which the amplitude of this cross-signal is larger, equal or lightly smaller than the P-wave and with almost the same frequency spectrum. In such cases, the atrial sense amplifier threshold and band-pass are not useful for R-cross-wave rejection, and this signal is transmitted to the pacer as if it were a second natural P-wave. Anti-cross-sensing logic circuit 54 (FIGS. 2 and 3) avoids this situation for any embodiments of this invention. The output of the comparator output stage (not shown) of the atrial sense amplifier 34 is inverted in a first NAND gate 56 and fed to a second NAND gate 58. The other input to gate 58 is from a 50 ms one-shot OS7 which is triggered by the output of ventricular sense amplifier 38, as shown. An atrial signal occuring contemporaneously with an R-wave is rejected by the logic of the second NAND gate. The 50 ms delay provided by OS7 is necessary because of the delay occuring at the output of the two sense amplifiers (including, as usual, analog comparators at their outputs) as a consequence of the difference in amplitude and pulsewidth of the signals at their inputs.

The foregoing circuits thus eliminate or greatly reduce crosstalk between bipolar pacing leads with a minimum of additional circuitry. Without using output transformers, cross sensing is prevented by isolating the input/output circuitry for the respective channels. By using the outputs of the sense amplifiers to trigger corresponding charging circuitry in the embodiment of FIG. 3, the capacitors can remain disconnected normally while additional timing circuitry to initiate the charging cycle is made unnecessary. Moreover, this system positively insures that stimulation on one channel is followed immediately with recharging of the respective power capacitor. By using a separate capacitor for the power supply for each input/output circuit associated with a given channel, the power supply for that channel is effectively isolated from the common reference potentials which in the past encouraged crosstalk between the bipolar leads. Thus, the well known advantages of bipolar leads in some situations can be obtained without the formerly attendant disadvantages of increased interchannel interference.

In addition, by using logic circuit 54, or by introducing the equivalent logic in the software of a microprocessor-based pacer, the invention avoids cross-sensed pulses in the atria produced by normal or abnormal ventricular activity being sensed by the pacer logic as normal P-waves and producing incorrect pacer decisions. Retrograde conduction and premature ventricular contractions are particular cases of such abnormal ventricular activity.

Figure 5:
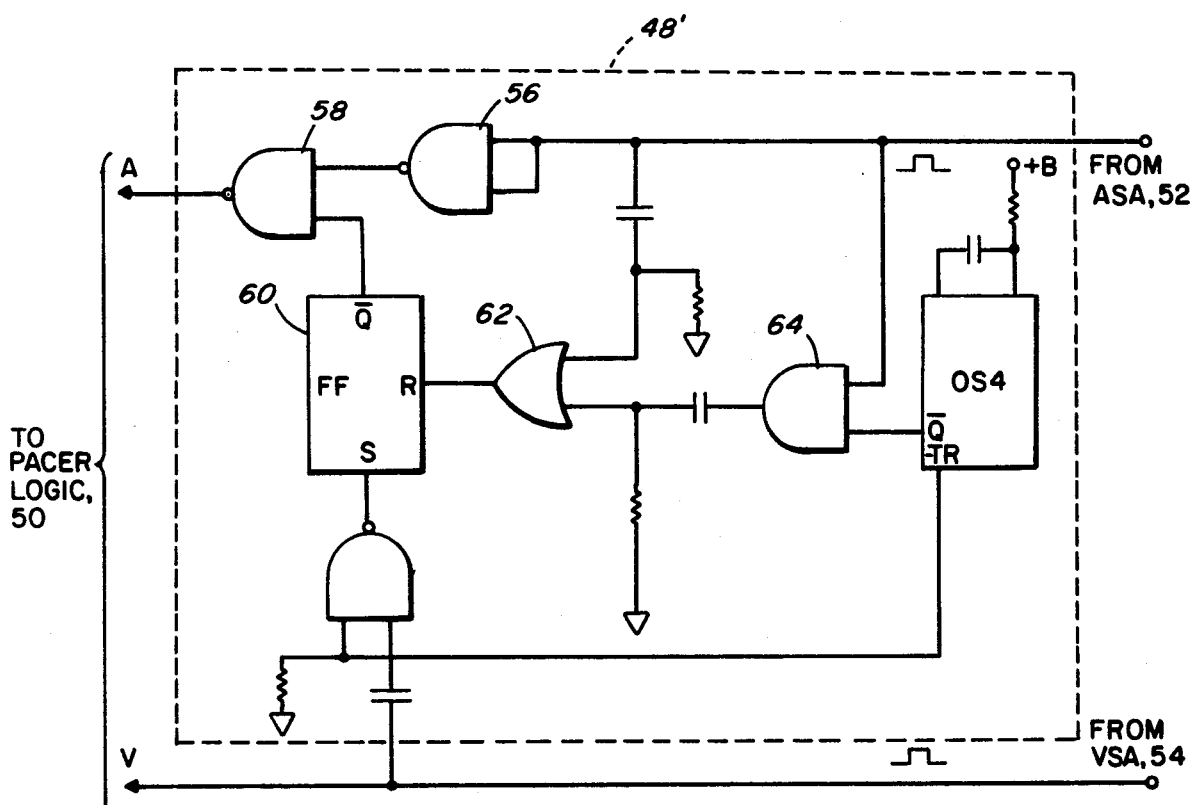
FIG. 5 is a schematic diagram of an alternate embodiment of the anti-cross-sensing logic circuit 54 of FIGS. 2 and 3.
Figure 6:
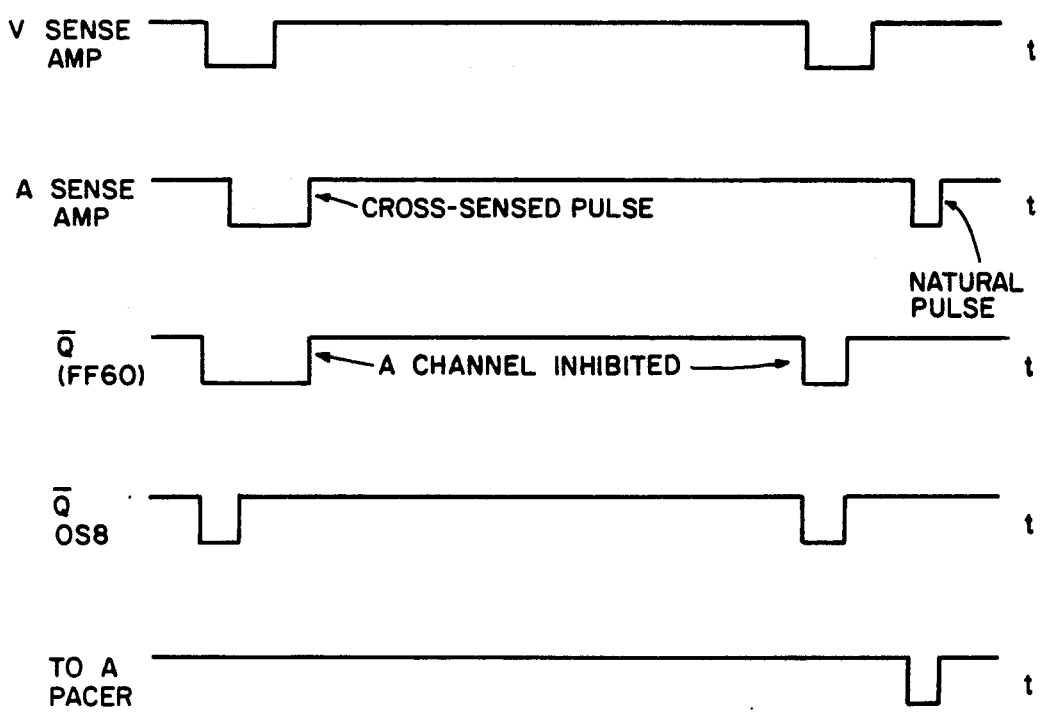
FIG. 6 is a timing diagram illustrating the relationship between typical signals in the circuit of FIG. 5.

The logic circuit 54 shown in FIGS. 2 and 3 can be replaced by the slightly different one, circuit 54', shown in FIG. 5. In the embodiment of FIG. 5, the inhibition of the A signal is initiated by the appearance of the V signal and is removed by the end of the A signal (the positive going edge of the A signal). This strategy is implemented by the latch 60 which is set by a negative going V signal from ventricular sense amplifier 38 and is reset via OR gate 62 by a positive going A signal. In the event that no cross-sensing is present while a V signal occurs (i.e., atrial sense amplifier output high), the timer OS8 resets the latch 60 after a short delay (10–30 ms). Due to gate 64 the timer has no effect if the output of the atrial sense amplifier is low (i.e., sensing) when the astable period of OS8 expires, as illustrated in FIG. 6.

Variations in the above described circuitry consistent with the fundamental principles may be made without departing from the spirit or scope of the invention. For example, the resistance values and specific timing intervals are only given by way of illustration and are not intended to limit the scope of the invention as defined by the appended claims and equivalents thereto.

What is claimed is:

1. A cardiac pacer of the type comprising a main power supply, two pacer leads for establishing electrical contact with different parts of the heart, dual channel input/output circuitry including two sense circuits providing logic outputs indicative of electrical activity associated with the respective leads and two stimulation output circuits responsive to logic commands for applying electrical stimulation pulses to the heart via the respective leads and pacing logic circuitry powered by said main power supply for providing logic commands to said stimulation output circuits and connected to receive the outputs of said sense circuits, wherein the improvement comprises:

means for electrically isolating the input/output circuitry including:

(a) first capacitive means for storing electrical energy connected across said input/output circuitry for one channel to supply power thereto;

(b) second capacitive means for storing electrical energy connected across the input/output circuitry for a second channel, and (c) means operatively connected to said main power supply for separately charging said first and second capacitive means and for isolating said input/output circuitry for the two channels from each other and from the main power supply, whereby crosstalk between said pacing leads is reduced.

2. The pacer of claim 1, wherein one of said leads is an atrial lead and the other lead is a ventricular lead, the respective sense circuits thus being atrial and ventricular sense circuits, the pacing logic circuitry having atrial and ventricular sense inputs, wherein the improvement further comprises an anti-cross-sensing logic circuit including latch means connected to be set by the beginning of an output pulse from the ventricular sense circuit, gate means responsive to the condition of said latch means connected between said atrial sense circuit and the atrial sense input to said pacing logic circuitry to pass the output of said atrial sense circuit thereto only when said latch means is in the reset condition, and means for resetting said latch means in response to the end of an output pulse from said atrial sense circuit and at the expiration of a predetermined period following the beginning of the last output pulse from the ventricular sense circuit if there is no output from the atrial sense circuit.

3. A cardiac pacer of the type comprising a main power supply, two pacing leads for establishing electrical contact with different parts of the heart, first and second input/output circuits associated respectively with said leads and defining respective channels and having means for producing electrical output stimulation to the heart via the respective lead and for producing a logic signal indicative of electrical activity on said lead and pacing logic circuitry energized directly by said main power supply connected to receive the logic outputs of said first and second input/output circuits for producing logic commands to said input/output circuits causing stimulation outputs therefrom, wherein the improvement comprises:

first and second power supplies for said first and second input/output circuits respectively separate from each other and from said main power supply, and means for at least periodically charging both said first and second power supplies from said main power supply to restore their energy level, whereby crosstalk between said leads is reduced.

4. The pacer of claim 3, wherein the improvement further comprises:

said power supplies including respectively first and second capacitive means for storing electrical energy connected across said input/output circuits respectively.

5. The pacer of claim 4, wherein said charging means includes first and second pairs of resistive elements connecting opposite sides of said first and second capacitive means respectively to opposite sides of said main power supply, whereby said capacitive means are continuously charged from said main power supply but isolated from each other by virtue of the interceding resistances.

6. The pacer of claim 5, wherein each of said resistive elements has a resistance value on the order of 15 kilohms.

7. The pacer of claim 6, wherein the capacitance of each said capacitive means is chosen such that the corresponding input/output circuit is capable of producing the maximum current output at the maximum desired rate.

8. The pacer of claim 5, wherein the improvement further comprises logic means connected between one of the input/output circuits and said pacing logic circuitry for blocking the sense logic output from said one input/output circuit in the presence of a sense logic output from the other input/output circuit.

9. The pacer of claim 4, wherein said charging means includes first and second pairs of electrical switches arranged to connect opposite sides of the respective capacitive means to said main power supply.

10. The pacer of claim 9, wherein said improvement further comprises:

electronic means for intermittently actuating said first and second pairs of switches to connect said capacitive means momemtarily to said main power supply for recharging.

11. The pacer of claim 10, wherein said actuating means includes first means responsive to the logic output of one input/output circuit for closing a corresponding pair of switches for a predetermined time interval.

12. The pacer of claim 11, wherein said actuating means includes second means responsive to the logic output of the other one of said input/output circuits for closing the other pair of said switches for a predetermined interval.

13. The pacer of claim 9, wherein the improvement further comprises:

a pair of resistive means connected from one side of each of said capacitive elements respectively to the reference potential side of said main power supply in parallel with the corresponding switch.

14. The pacer of claim 13, wherein the improvement further comprises a pair of switch means in series with said resistive elements, respectively, for interrupting the connection to the reference potential side of said power supply whenever the capacitive means for the opposite channel is charging.

15. The pacer of claim 4, wherein said charging means includes first and second pairs of switches for connecting respective sides of said first and second capacitive means to corresponding sides of said main power supply, and means for intermittently actuating at least one of said pairs of switches at a time for a predetermined interval to charge the respective capacitive means.

16. The pacer of claim 15, wherein said improvement further comprises means for referencing the logic level associated with each of said input/output circuits to the reference potential of said main power supply.

17. The pacer of claim 15, wherein said referencing means includes resistive elements connected in parallel with the corresponding switch connecting the respective capacitive element to the reference potential side of said main power supply.

18. The pacer of claim 15, wherein said charging means includes means responsive to a logic output from one of said input/output circuits for actuating a corresponding pair of said switches for a predetermined interval of time to charge the corresponding capacitive means.

19. The pacer of claim 15, wherein said charging means includes a pair of charging logic circuit means each responsive to a sense logic output from a corresponding input/output circuit for actuating a corresponding pair of switches after a predetermined delay for a predetermined interval of time following which said charging logic circuit means is refractory for a predetermined interval.

20. The pacer of claim 15, wherein the improvement further comprises logic means connected between one of the input/output circuits and said pacing logic circuitry for blocking the sense logic output from said one input/output circuit in the presence of a sense logic output from the other input/output circuit.

21. Anti-cross-sensing circuitry for a cardiac pacer having atrial and ventricular leads, means for applying stimulation pulses via said leads, atrial and ventricular sense circuits producing a digital output pulse in response to defined electrical activity on the respective lead, and pacing logic circuitry having atrial and ventricular sense inputs connected to said sense circuits for issuing appropriate stimulation commands for cardiac pacing, comprising latch means connected to be set by the beginning of an output pulse from the ventricular sense circuit, gate means responsive to the condition of said latch means connected between said atrial sense circuit and the atrial sense input to said pacing logic circuitry to pass the output of said atrial sense circuit thereto only when said latch means is in the reset condition, and means for resetting said latch means in response to the end of an output pulse from said atrial sense circuit and at the expiration of a predetermined period following the beginning of the last output pulse from the ventricular sense circuit if there is no output from the atrial sense circuit.

* * * * *